(12) United States Patent
Cone et al.

(10) Patent No.: US 9,744,171 B2
(45) Date of Patent: Aug. 29, 2017

(54) POSITIVE ALLOSTERIC MODULATORS FOR MELANOCORTIN RECEPTORS

(71) Applicant: Vanderbilt University, Nashville, TN (US)

(72) Inventors: Roger D. Cone, Nashville, TN (US); Julien A. Sebag, Nashville, TN (US); Jacques Pantel, Paris (FR); Savannah Y. Williams, Nashville, TN (US); David C. Weaver, Franklin, TN (US); Gary A. Sulikowski, Brentwood, TN (US); Craig W. Lindsley, Brentwood, TN (US); Padma S. Portonova, Brentwood, TN (US); Chao Zhang, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/383,715

(22) PCT Filed: Mar. 6, 2013

(86) PCT No.: PCT/US2013/029353
§ 371 (c)(1),
(2) Date: Sep. 8, 2014

(87) PCT Pub. No.: WO2013/134376
PCT Pub. Date: Sep. 12, 2013

(65) Prior Publication Data
US 2015/0018371 A1    Jan. 15, 2015

Related U.S. Application Data

(60) Provisional application No. 61/607,329, filed on Mar. 6, 2012.

(51) Int. Cl.
| | | |
|---|---|---|
| *A61K 31/4965* | (2006.01) |
| *A61K 31/519* | (2006.01) |
| *A61K 31/4192* | (2006.01) |
| *C07D 231/08* | (2006.01) |
| *C07D 333/38* | (2006.01) |
| *C07D 401/12* | (2006.01) |
| *C07D 403/04* | (2006.01) |
| *C07D 409/12* | (2006.01) |
| *C07D 417/12* | (2006.01) |
| *C07D 249/06* | (2006.01) |
| *C07D 471/04* | (2006.01) |
| *C07D 487/04* | (2006.01) |
| *C07D 491/04* | (2006.01) |
| *C07D 495/04* | (2006.01) |
| *C07D 277/18* | (2006.01) |
| *C07D 277/54* | (2006.01) |

(Continued)

(52) U.S. Cl.
CPC .......... *A61K 31/519* (2013.01); *A61K 31/166* (2013.01); *A61K 31/216* (2013.01); *A61K 31/343* (2013.01); *A61K 31/381* (2013.01); *A61K 31/4045* (2013.01); *A61K 31/415* (2013.01); *A61K 31/4152* (2013.01); *A61K 31/4162* (2013.01); *A61K 31/4192* (2013.01); *A61K 31/426* (2013.01); *A61K 31/427* (2013.01); *A61K 31/436* (2013.01); *A61K 31/437* (2013.01); *A61K 31/4355* (2013.01); *A61K 31/47* (2013.01); *A61K 31/4704* (2013.01); *A61K 31/4709* (2013.01); *A61K 31/4741* (2013.01); *A61K 31/495* (2013.01); *A61K 31/496* (2013.01); *A61K 31/506* (2013.01); *A61K 31/517* (2013.01); *C07D 209/16* (2013.01); *C07D 231/08* (2013.01); *C07D 249/06* (2013.01); *C07D 277/18* (2013.01); *C07D 277/54* (2013.01); *C07D 295/12* (2013.01); *C07D 307/82* (2013.01); *C07D 333/38* (2013.01); *C07D 401/12* (2013.01); *C07D 403/04* (2013.01); *C07D 409/12* (2013.01); *C07D 417/12* (2013.01); *C07D 471/04* (2013.01); *C07D 487/04* (2013.01); *C07D 491/04* (2013.01); *C07D 495/04* (2013.01); *G01N 33/502* (2013.01); *G01N 2333/46* (2013.01); *G01N 2500/10* (2013.01)

(58) Field of Classification Search
None
See application file for complete search history.

(56) References Cited

U.S. PATENT DOCUMENTS

2007/0149562 A1    6/2007 Braun et al.
2009/0312345 A1    12/2009 Fan et al.
(Continued)

OTHER PUBLICATIONS

Chandrika et al. (European Journal of Medicinal Chemistry, 2008, 43, 846-852).*
PCT International Search Report corresponding to PCT/US2013/029353, mailed Jun. 21, 2013, pp. 1-13.
PubChem website, http://pubchem.ncbi.nlm.nih.gov/summary/summary.cgi?cid=741095&loc=ec_rcs, accessed Jun. 6, 2013.
Pantel, Jacques, et al. "Development of a high throughput screen for allosteric modulators of melanocortin-4 receptor signaling using a real time cAMP assay." European journal of pharmacology 660.1 (2011): 139-147.

(Continued)

*Primary Examiner* — Dennis Heyer
*Assistant Examiner* — Daniel M Podgorski
(74) *Attorney, Agent, or Firm* — Tarolli, Sundheim, Covell & Tummino LLP (57) ABSTRACT

Positive allosteric modulators of melanocortin receptors, especially allosteric potentiators of the receptors MC3R and MC4R are described herein. Also provided are pharmaceutical compositions containing the positive allosteric modulators and methods of treating obesity or an obesity-related disorder such as type 2 diabetes, comprising administering an effective amount of the positive allosteric modulator.

10 Claims, 6 Drawing Sheets

(51) Int. Cl.

| | |
|---|---|
| C07D 209/16 | (2006.01) |
| C07D 295/12 | (2006.01) |
| C07D 307/82 | (2006.01) |
| A61K 31/343 | (2006.01) |
| A61K 31/381 | (2006.01) |
| A61K 31/415 | (2006.01) |
| A61K 31/4162 | (2006.01) |
| A61K 31/427 | (2006.01) |
| A61K 31/437 | (2006.01) |
| A61K 31/4704 | (2006.01) |
| A61K 31/4709 | (2006.01) |
| A61K 31/4741 | (2006.01) |
| A61K 31/495 | (2006.01) |
| A61K 31/496 | (2006.01) |
| A61K 31/506 | (2006.01) |
| A61K 31/517 | (2006.01) |
| A61K 31/166 | (2006.01) |
| A61K 31/216 | (2006.01) |
| A61K 31/4045 | (2006.01) |
| A61K 31/4152 | (2006.01) |
| A61K 31/426 | (2006.01) |
| A61K 31/4355 | (2006.01) |
| A61K 31/436 | (2006.01) |
| A61K 31/47 | (2006.01) |
| G01N 33/50 | (2006.01) |

(56) References Cited

U.S. PATENT DOCUMENTS

2010/0087468 A1    4/2010   Zhu et al.
2010/0311648 A1    12/2010   Dodd et al.

OTHER PUBLICATIONS

Ellacott, Kate LJ, and Roger D. Cone. "The role of the central melanocortin system in the regulation of food intake and energy homeostasis: lessons from mouse models." Philosophical Transactions of the Royal Society of London B: Biological Sciences 361.1471 (2006): 1265-1274.

Srisai, Dollada, et al. "Characterization of the hyperphagic response to dietary fat in the MC4R knockout mouse." Endocrinology 1523 (2011): 890-902.

Song, Youngsup, and Roger D. Cone. "Creation of a genetic model of obesity in a teleost." The FASEB Journal 21.9 (2007): 2042-2049.

Zhang, Chao, Paul M. Forlano, and Roger D. Cone. "AgRP and POMC neurons are hypophysiotropic and coordinately regulate multiple endocrine axes in a larval teleost." Cell metabolism 152 (2012): 256-264.

Levi, Carrolla, Joanne Voisey, and Angela Van Daal. "Mouse models of obesity." Angela van Daal (2004): 2.

* cited by examiner

POSITIVE ALLOSTERIC MODULATORS FOR MELANOCORTIN RECEPTORS

CROSS-REFERENCE TO RELATED APPLICATIONS

This application is a national phase application of, claims priority to, and any other benefit of, International Application No.: PCT/US2013/029353, filed on Mar. 6, 2013, and entitled POSITIVE ALLOSTERIC MODULATORS FOR MELANOCORTIN RECEPTORS, which claims priority to, and any other benefit of U.S. Provisional Application No. 61/607,329, filed on Mar. 6, 2012, both of which are hereby incorporated by reference in their entirety.

TECHNICAL FIELD

The present disclosure generally relates to compositions and methods for treating obesity and obesity-related disorders, and more particularly to the use of positive allosteric modulators of melanocortin receptors.

BACKGROUND

The adipostat is the mechanism by which the brain detects and maintains constant levels of energy stored in adipocytes in the form of lipids. Key elements of the adipostat include the adipocyte-derived hormone leptin that is expressed in proportion to energy levels and serves to communicate this information to the central nervous system and the central circuits, which sense and respond to leptin. Blockade of one of these circuits, the central melanocortin system, disrupts leptin action, as well as a variety of acute physiological systems involved in energy intake and expenditure, and causes a distinct obesity syndrome in mice and humans, characterized by increased adiposity as well as increased linear growth.

The melanocortin circuitry of the central nervous system (CNS) is a critical component of the adipostat. Srisai et al., Endocrinology, 152(3): 890-902 (2011). Activation of these circuits inhibits food intake and stimulates energy expenditure. The melanocortin-4 receptor (MC4R) is a major component of the machinery controlling food intake and energy expenditure. Consequently, MC4R haploinsufficiency due to mutations in the receptor is responsible for up to 5% of early onset obesity. For this reason, MC4R has been a target of the major pharmaceutical companies for the development of drugs for the treatment of common obesity. The first clinical trials of potent MC4R agonists, however, failed due to pressor activity.

The MC4R, a G-protein coupled receptor (GPCR), couples through Gs and upon agonist binding promotes cAMP production and ERK1/2 mitogen-activated protein kinase phosphorylation. Potent orthosteric agonists can activate GPCR signaling in magnitude and in temporo-spatial patterns that exceed those exhibited under normal physiological patterns of activation. Such orthosteric agonists may thus tend to induce side effects. During the past decade, allosteric modulators have provided a successful alternative to conventional orthosteric agents, albeit for indications other than obesity.

SUMMARY

In one aspect, pharmaceutical compositions including a positive allosteric modulator for a melanocortin receptor together with a pharmaceutically acceptable carrier are provided. In some embodiments, the positive allosteric modulator is an in vivo activator of the MC4R, while in other embodiments the positive allosteric modulator is a β-arresting blocker.

In another aspect, methods of activating a melanocortin receptor by positive allosteric modulation are described. In one embodiment, the method includes contacting a melanocortin receptor with a positive allosteric modulator compound, while in another embodiment the method includes contacting a melanocortin receptor with a positive allosteric modulator compound to block coupling of a melanocortin receptor to β-arrestin.

In another aspect, a method for treating obesity or an obesity-related disorder in a subject is provided that includes administering a therapeutically effective amount of a pharmaceutical composition including a positive allosteric modulator for a melanocortin receptor together with a pharmaceutically acceptable carrier. In some embodiments, the obesity or obesity-related disorder is mediated by dysfunctional melanocortin receptor signaling, while in further embodiments the disorder is mediated by dysfunctional melanocortin-4 receptor (MC4R) signaling.

BRIEF DESCRIPTION OF THE FIGURES

The present invention may be more readily understood by reference to the following drawings.

FIG. 2 provides graphic examples of the pharmacological analyses used to identify small molecule positive allosteric modulators of the MC4R. Curves show real-time measurement of cAMP production in the MC4R-GLO cell line, as reported by luciferase luminescence, following successive treatments with small molecule compounds (first arrow), or doses indicated of α-MSH or isoproterenol (second arrow). Luminescence recording was performed in 384 well plates using a Hammamatsu FDSS6000 plate reader at 37° C. for 26 min. Luminescence is reported as the average of quadruplicates±SEM for a representative experiment. Real-time recording of cAMP production in MC4R-GLO cells (left panel) or β2AR-GLO cells (right panel) treated with the indicated ligands: EC100 dose of α-MSH or isoproterenol (heavy black traces), EC20 dose of α-MSH or isoproterenol (medium density traces), or a combination of the native ligand plus 10 µM drug (light trace).

FIG. 3 provides a pharmacological characterization of MC4R PAMS. (A) Example of the ability of a typical MC4R PAM (compound C, 10 uM) to increase the responsiveness of the hMC4R to graded doses (indicated) of α-MSH. (B) Concentration response curves for compound A on MC4R expressing cells in the presence of a submaximal concentration of the melanocortin agonist α-MSH. (C) Traces of cAMP response in MC3R and MC4R expressing cells in the presence of increasing concentrations of three representative compounds displaying different degrees of specificity for allosteric modulation of two closely related melanocortin receptors.

As demonstrated previously in Zhang et al. (Cell Metab. 15, 256-264, 2012), the MC4R regulates the linear growth of zebrafish larvae from 0-5 days post-fertilization, with activation of the receptor inhibiting growth. In this assay, the ability of the MC4R PAM compounds indicated to activate the MC4R and inhibit growth is tested by treating wild type zebrafish and MC4R–/– zebrafish with drug. Bars indicate the mean and standard error of length for approximately 45 larvae in each condition. For detailed protocol conditions, see Zhang et al. Briefly, 45 live embryos were transferred into single wells of a 12-well cell culture plate in 4 ml fresh egg water. 10 mM stock compound solutions were prepared in 100% DMSO. A 4 µL compound solution or 40 µL peptide solution was added and mixed into each well to make 10 µL final concentration with 0.1% DMSO. Wells with 0.1% DMSO or 10 µM α-MSH were included as vehicle or positive controls, respectively. Compound/peptide solutions were changed daily. Embryos were raised under standard light/dark cycle at 28° C. At 5 dpf (days post fertilization), fish were anaesthetized in 0.4% Tricaine solution and the linear body lengths (forehead to trunk terminus) of 30-35 fish from each well were measured using the axiovision (Ver3.1) digital micrometer with a StemiSV11 Dissecting Microscope (Carl Zeiss INC,). Prism 5.0 was used for the interpretation and analysis of all measurements. α-MSH=the endogenous agonist of the MC4R; NDP-MSH=a potent synthetic peptide agonist of the MC4R; THIQ=a small molecule orthosteric agonist of the MC4R.

DETAILED DESCRIPTION

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

Definitions

As used herein, the term "organic group" is used to mean a hydrocarbon group that is classified as an aliphatic group, cyclic group, or combination of aliphatic and cyclic groups (e.g., alkaryl and aralkyl groups). In the context of the present invention, suitable organic groups for compounds are those that do not interfere with the positive allosteric modulation activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms). Particular alkyl groups can be abbreviated by well-known abbreviates; e.g., Me for methyl and Et for ethyl.

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The tem "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N, The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. This is true regardless of whether or not the enantiomers are shown in chemical formula representing the compounds. For example, if a compound that includes a chiral center is shown without any indication of stereochemistry, it is presumed to represent all possible stereoisomers of the compound. It should be understood that the term "compound" includes any or all of such forms, whether explicitly stated or not (although at times, "salts" are explicitly stated).

As used herein, the term "therapeutically effective amount" can refer to that amount of a positive allosteric modulator or composition thereof that results in amelioration of symptoms or a prolongation of survival in a subject. A therapeutically relevant effect relieves to some extent one or more symptoms of a medical condition (e.g., obesity or an obesity-related disorder) or returns to normal either partially or completely one or more physiological or biochemical parameters (e.g., an MC4R signaling pathway) associated with or causative of the medical condition.

As used herein, the term "subject" can refer to any animal including, but not limited to, humans and non-human animals (e.g., rodents, arthropods, insects, fish (e.g., zebrafish), non-human primates, ovines, bovines, ruminants, lagomorphs, porcines, caprines, equines, canines, felines, birds, etc.), which is to be the recipient of a particular treatment. Typically, the terms "patient" and "subject" are used interchangeably herein in reference to a human subject.

As used herein, the term "melanocortin receptor" can refer to any member of the family of melanocortin receptors including melanocortin-1 receptor (MC1R), melanocortin-2 receptor (MC2R), melanocortin-3 receptor (MC3R), melanocortin-4 receptor (MC4R), and melanocortin-5 receptor (MC5R).

As used herein, the term "allosteric modulator" can refer to a compound that does not bind to an orthosteric ligand binding site of a melanocortin receptor, but instead acts elsewhere to modulate melanocortin receptor function or activity. Binding by an allosteric modulator does not trigger a functional activity in the absence of the orthosteric ligand (e.g., a melanocortin receptor agonist). A positive allosteric modulator (PAM) is a compound that amplifies the effect of an orthosteric ligand.

As used herein, the term "modulate" can refer to a change in the biological activity of a biologically active molecule (e.g., a melanocortin receptor). Modulation can be an increase or a decrease in activity, a change in binding characteristics, or any other change in the biological, functional, or immunological properties of a biologically active molecule.

As used herein, the term "activity" with reference to melanocortin receptor activity can refer to a cellular, biological, and/or therapeutic activity or function of a melanocortin receptor. Examples of such activities can include, but are not limited to, signal transduction, interacting with binding partner(s) or cellular component(s), and modulating cellular responses to stimuli.

As used herein, the term "agonist" can refer to a molecule or compound which, when interacting with a biologically active molecule (e.g., a melanocortin receptor), causes a change (e.g., enhancement) in the biologically active molecule, which modulates the activity of the biologically active molecule. A variety of melanocortin receptor agonists are known. See Nargund et al., J Med. Chem. 49: 4035-43 (2006). Examples of MC4R selective agonists include beta-MSH, THIQ, and PF-00446687, as well as the endogenous agonist αMSH.

As used herein, the terms "treating" or "treatment" of a medical condition (e.g., obesity or an obesity-related disorder) can include: (1) preventing at least one symptom of the disease, i.e., causing a clinical symptom to not significantly develop in a subject that may be exposed to or predisposed to the condition but does not yet experience or display symptoms of the condition; (2) inhibiting the disease, i.e., arresting or reducing the development of the condition or its symptoms; or (3) relieving the condition, i.e., causing regression of the condition or its clinical symptoms. Treatment, prevention, and ameliorating obesity or an obesity-related disorder, as used herein, can include, for example, weight loss and/or decreasing insulin resistance associated with the condition.

Figure 1:
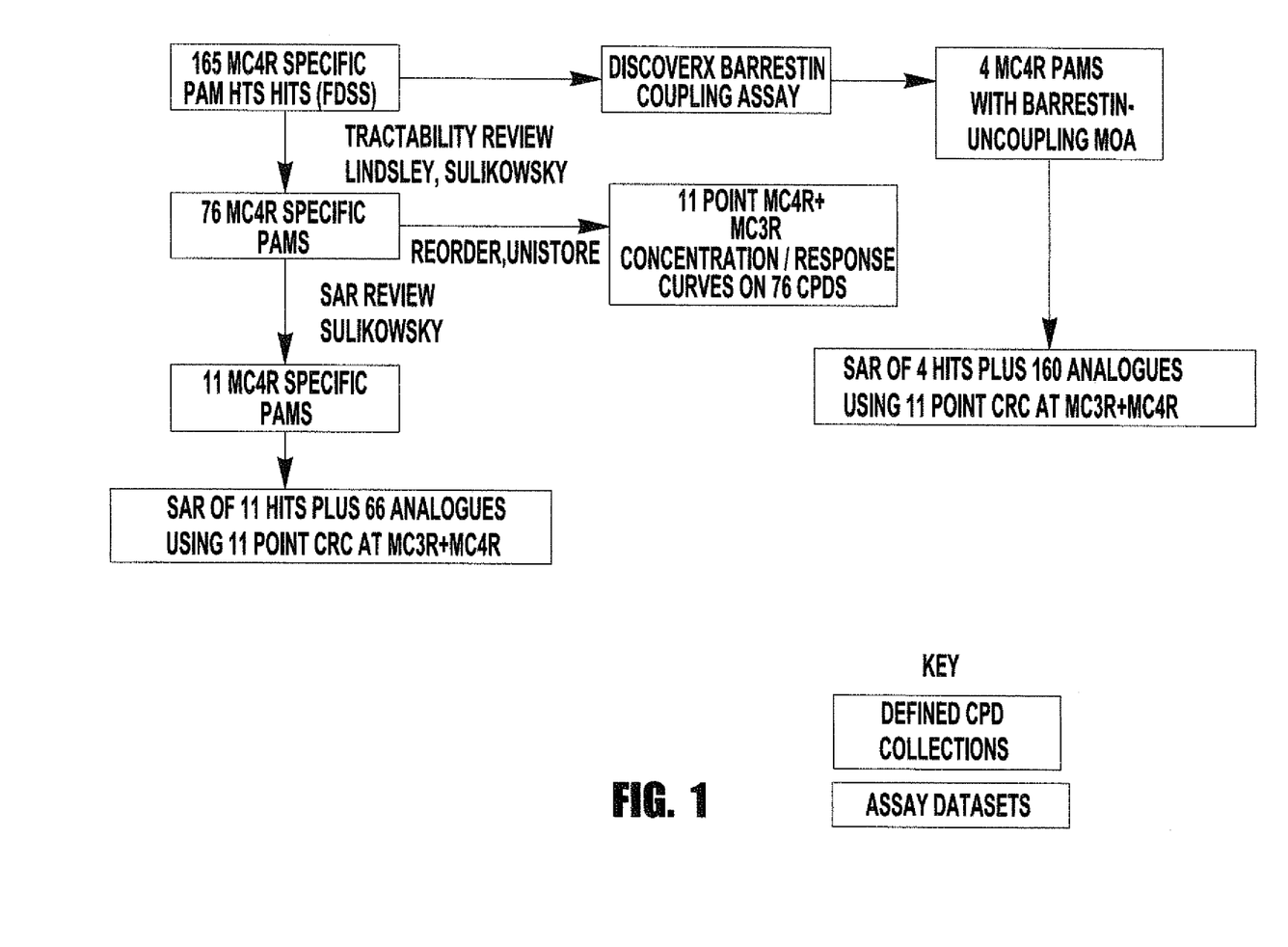
FIG. 1 provides a schematic flow chart showing the 165 positive allosteric modulators of the MC4R, and the pharmacological and in vivo characterization of subsets thereof.
Figure 2:
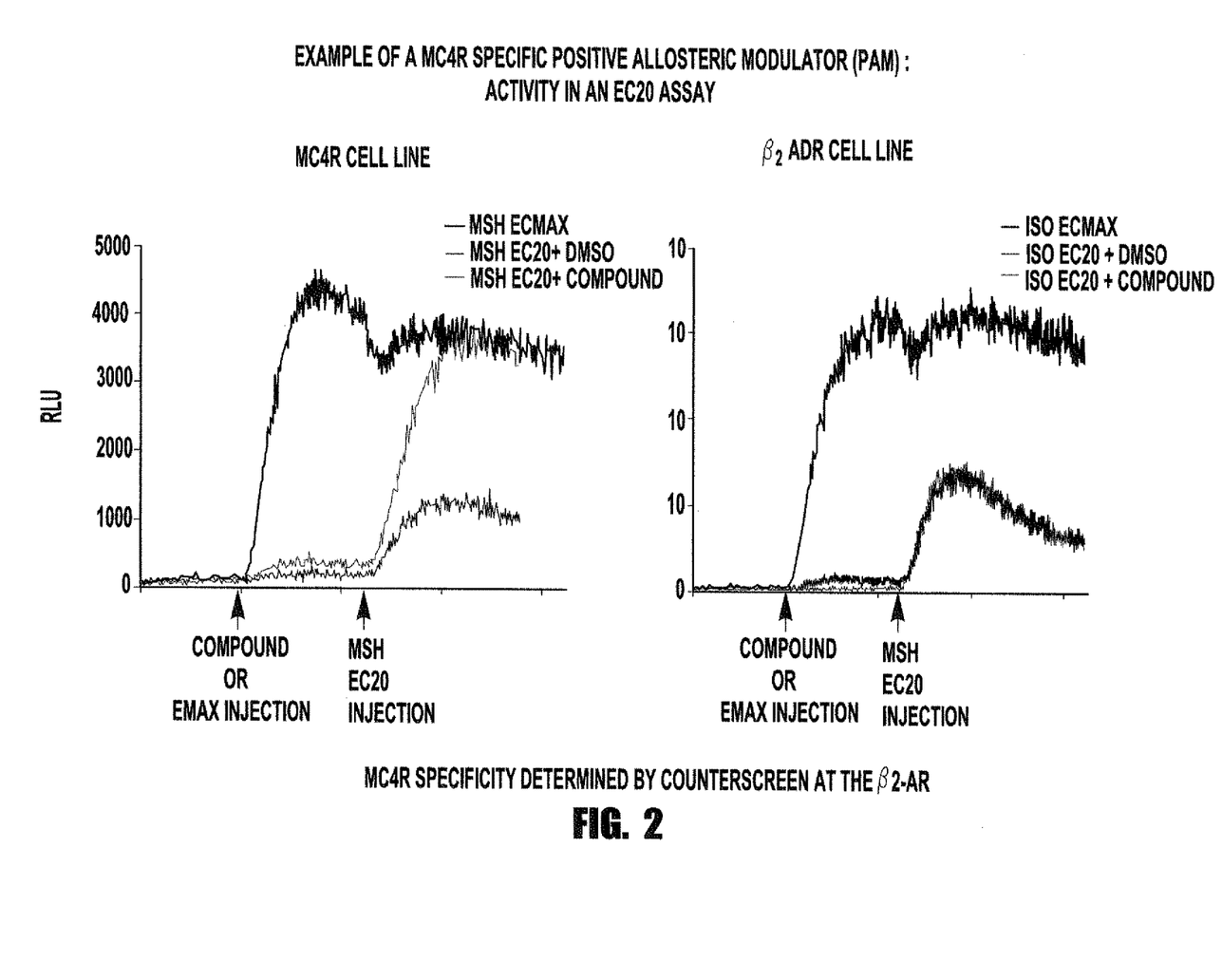
Figure 3:
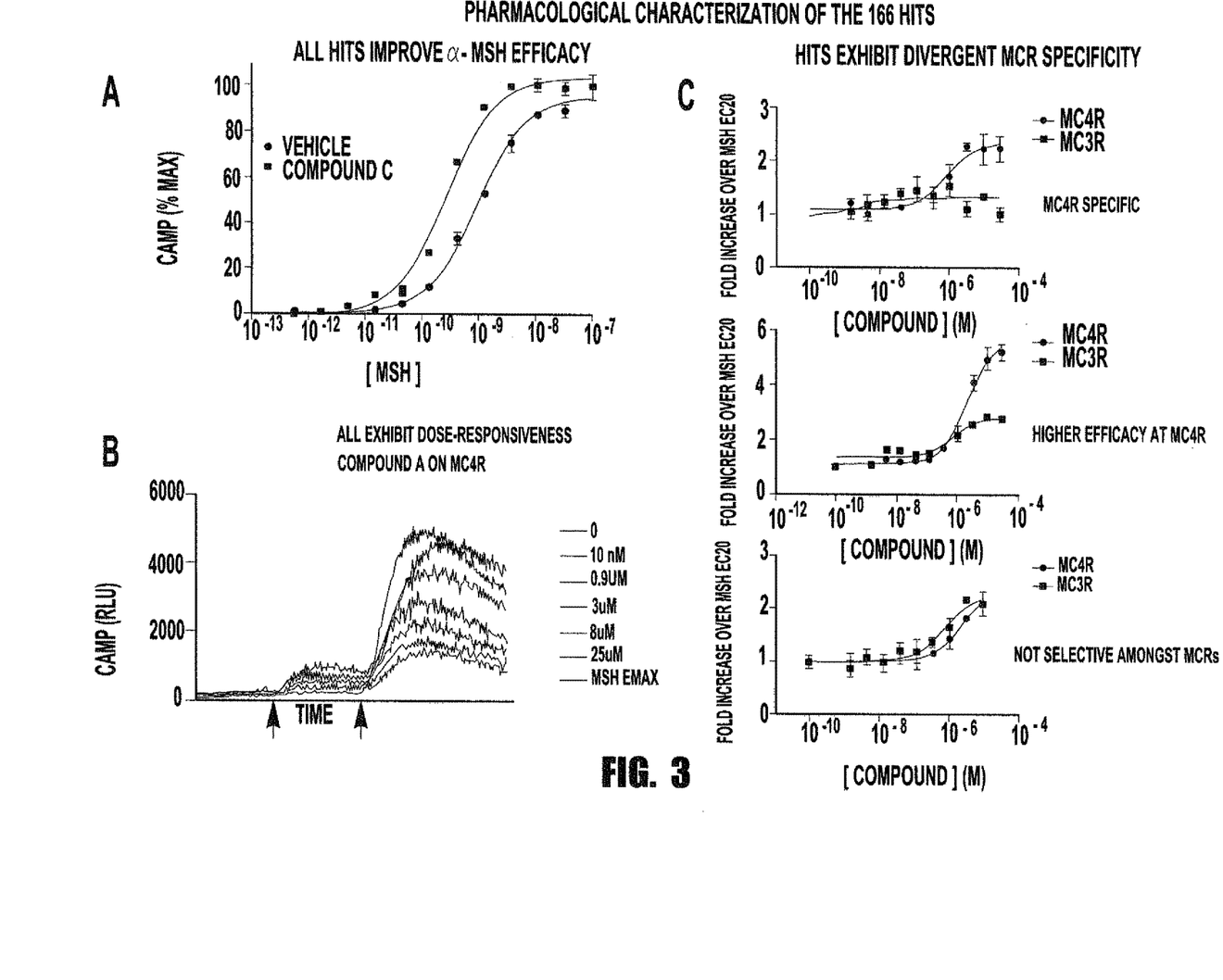

Positive allosteric modulators of melanocortin receptors were identified by following the drug discovery program outlined in FIG. 1. Briefly, a real-time cAMP high through-put-screening assay for allosteric modulators of the MC4R was used to identify 2472 positive allosteric modulators, which were then counter-screened at the β2-adrenergic receptor to yield 165 MC4R-specific allosteric modulators. Examples showing the results from positive allosteric modulators are shown in FIGS. 2 and 3. Of the 165 positive allosteric modulators, 76 were validated with 12-point concentration-response curves at the human MC3R and human MC4R. Both MC4R-specific and dual MC3R/MC4R positive allosteric modulators were identified. A 600 compound structure-activity relationship was then performed around a subset of 11 of the 76 positive allosteric modulators. Subsets of the 76 positive allosteric modulators were also analyzed using assays for the pharmacological mechanism(s) of action, including: (1) effects of the amplitude and kinetics of the $EC_{100}$ response to α-melanocyte-stimulating hormone (αMSH); (2) receptor affinity using europium-labeled Nle4-DPhe7-α-MSH (NDP-MSH); (3) cell surface receptor density using a tagged immunoprecipitable receptor; and (4) receptor densitization using a β-arrestin recruitment assay. These assays demonstrated that the tested positive allosteric modulators fall into certain mechanistic classes. For example, these assays demonstrated that: (1) certain positive allosteric modulators inhibit β-arrestin recruitment and, thus, work by blocking desensitization of the MC4R; (2) certain positive allosteric modulators have MC4R-specific activity; and (3) certain positive allosteric modulators depolarize MC4R neurons.

Based at least in part on these discoveries, the present disclosure provides positive allosteric modulators of melanocortin receptors. In addition, based on the role played by melanocortin receptors in energy homeostasis, a method for treating obesity or an obesity-related disorder (e.g., severe obesity caused by melanocortin obesity syndrome) is also provided. Although it is not necessary to understand the mechanisms in order to practice the present disclosure, and it is not intended that the present disclosure be limited based on the mechanisms described herein, it is believed that the positive allosteric modulators disclosed herein can increase melanocortin sensitivity to melanocortin receptor agonists (e.g, endogenous αMSH) to selectively modulate G protein-coupled receptor (GPCR) signaling pathways that regulate body weight versus blood pressure. It is further believed that selective modulation of such GPCR signaling pathways may be the result of positive allosteric modulators that increase agonist efficacy at melanocortin receptors (e.g., MC4R) by (1) inhibiting receptor desensitization (e.g., inhibiting coupling to β-arrestin) and/or (2) activating G protein coupling without blocking receptor desensitization.

In an aspect of the present disclosure, positive allosteric modulators of a melanocortin receptor (e.g., MC4R) are provided, as well as analogs, homologs, and pharmaceutically acceptable salts thereof. Homologs are compounds that form a part of a series, differing from one another by the successive addition of the same chemical moiety, e.g. a —CH$_2$— moiety. For example, ethanol (CH$_3$CH$_2$OH) and n-propanol (CH$_3$CH$_2$CH$_2$OH) are homologous alcohols. Analog compounds, on the other hand, typically have structurally similar nuclei but will differ in a particular chemical moiety. For example, alcohols and esters represent analogs, differing in the presence of a hydrogen and an alkyl group.

As positive allosteric modulators of a melanocortin receptor (e.g., MC4R) having the aforementioned effects, the compounds having the following structures may be useful in treating a subject having obesity or an obesity-related disorder, such as severe or morbid obesity associated with dysfunctional melanocortin signaling (e.g., melanocortin obesity syndrome due to MC4R-haploinsufficiency). The active compounds identified by inventors are collectively referred to as positive allosteric modulators. In one aspect of the present disclosure, the positive allosteric modulators can comprise a positive allosteric modulator for a melanocortin receptor selected from the group consisting of:

VU 034366

VU 122715

VU 132474

VU 0032360

VU 0060434

VU 049470

VU 123825

VU 0076742

VU 0098155

VU 0075721

VU 0093951

VU 0108201

VU 097964

VU 0117457

VU 011849

VU 080658 and analogs, homologs, and pharmaceutically acceptable salts thereof. These compounds are defined herein as the compounds of group I.

In another aspect, the positive allosteric modulators can comprise a growth inhibiting compound selected from the group consisting of

VU 0016415

VU 063674

VU 0050692

VU 0101245

VU 016351

VU 0110165

VU 0110240

VU 073033

VU 0146653 and analogs, homologs, and pharmaceutically acceptable salts thereof. These compounds are defined herein as the compounds of group II.

In a further aspect, the positive allosteric modulators can comprise a β-arrestin blocker selected from the group consisting of:

VU 0095934

VU 0127431

VU 0128769

VU 0055768

VU 117214

VU 067443

VU 039971

VU 0129839

VU 0129839

VU 0129567

VU 0131532 and analogs, homologs, and pharmaceutically acceptable salts thereof. These compounds are defined herein as the compounds of group III.

The positive allosteric modulators of groups I, II, and III are capable of further forming both pharmaceutically acceptable acid addition and/or base salts. All of these forms are within the scope of the present disclosure, and can be orally administered (e.g., by chronic daily dosing) to a subject to treat a disease mediated by dysfunctional melanocortin receptor signaling.

Pharmaceutically acceptable acid addition salts of the present disclosure can include, but are not limited to, salts derived from nontoxic inorganic acids such as hydrochloric, nitric, phosphohoric, sulfuric, hydrobromic, hydriodic, hydrofluoric, phosphorous, and the like, as well as the salts derived forth nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts can thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, malcate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like, as well as gluconate, galacturonate, and n-methyl glutamine.

Pharmaceutically acceptable base addition salts can be formed with metals or amides, such as alkali and alkaline earth metals or organic amines. Examples of metals used as cations include, but are not limited to, sodium, potassium, magnesium, calcium, and the like. Examples of suitable amines include, but are not limited to, $N_2$—N'-dibenzylethylenediamine, chloroprocaine, choline, diethanolamine, dicyclohexylamine, ethylenediamine, N-methylglucamine and procaine.

Certain of the compounds of the present invention can exist in unsolvated forms as well as solvated forms, including, but not limited to, hydrated forms. In general, the solvated forms, including hydrated forms, can be equivalent to unsolvated forms and are intended to be encompassed within the scope of the present disclosure.

Administration and Formulation of Positive Allosteric Modulators

Pharmaceutically acceptable carriers for the positive allosteric modulators described herein can be in any suitable form (e.g., solids, liquids, gels, etc.). A solid carrier can be one or more substances, which may also act as diluents, flavoring agents, binders, preservatives, and/or an encapsulating material. For example, positive allosteric modulators (or any analog or homolog thereof) can be administered to a subject in a pharmaceutical composition at a therapeutically effective amount and for a period of time effective to increase melanocortin receptor sensitivity to a melanocortin receptor agonist (as compared to a control). Pharmaceutically acceptable carriers are known in the art, and may include any material(s) that is not biologically or otherwise undesirable, i.e., the material may be incorporated into or added to the positive allosteric modulator(s) without causing any undesirable biological effects or interacting in a deleterious manner with any of the other components of the composition. When the term "pharmaceutically acceptable" is used to refer to a pharmaceutical carrier, it can be implied that the carrier has met the required standards of toxicological and manufacturing testing or that it is included on the Inactive Ingredient Guide prepared by the U.S. Food and Drug administration.

The dose, amount, and/or quantity of a positive allosteric modulator, or any analog or homolog thereof, administered to the subject can depend on the specific positive allosteric modulator selected. It will be appreciated that the dosage amounts used will depend on the potency of the specific positive allosteric modulator (or analog or homolog thereof) and the therapeutic regimen employed. Determination of a therapeutically effective amount is within the capability of those skilled in the art. The exact formulation, route of administration, and dosage can be chosen by a medical professional, for example, in view of the subject's disease. It should also be understood that a "therapeutically effective amount" may be interpreted as an amount giving a desired therapeutic effect, whether taken in one dose or in any number of doses, or taken alone or in combination with other compounds. In the case of the present disclosure, a "therapeutically effective amount" may be understood as an amount of one or more positive allosteric modulators described herein required to treat a disease mediated by dysfunctional melanocortin receptor signaling.

Candidate agents may be tested in animal models. Typically, the animal model is one for the study of obesity or an obesity-related disorder. The study of obesity in animal models (for instance, mice) is a commonly accepted practice for the determining the effectiveness of compounds in humans. See Carroll et al., Clin Dermatol., 22(4): 345-9 (2004). For example, Zucker Fatty, ZDF, GK rats, ob/ob & db/db mice are all known to be genetic models for obesity. Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the obesity, including, for instance, diabetes, hypertension, and fatty liver disease, or combinations thereof.

The location(s) where the positive allosteric modulator(s) and/or composition is/are administered may be determined based on the subject's individual need, such as the particular type of disease. For example, the positive allosteric modulator(s) and/or composition may be administered to the subject in an orally bioavailable form. It will be appreciated that other routes of administration can be used, such as injection (e.g., intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and infrasternal routes).

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated compounds can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound of the invention (i.e., active agent) is such that the dosage level will be effective to produce the desired result in the subject.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Treatment of Obesity and Obesity-Related Disorders using Positive Allosteric Modulators A method for treating obesity or an obesity-related disorder in a subject is provided that includes administering a therapeutically effective amount of a pharmaceutical composition including a positive allosteric modulator of melanocortin receptors to the subject. The positive allosteric modulator can be any of the melanocortin receptor affecting compounds described herein. The at least one positive allosteric modulator can be administered in an amount effective to increase melanocortin receptor sensitivity to a melanocortin agonist (e.g., endogenous αMSH) as compared to a control. The at least one positive allosteric modulator can include any one or combination of the compounds of groups I, II, or III.

In another aspect, medical conditions treatable by administering a therapeutically effective amount of at least one positive allosteric modulator can include obesity and obesity-related disorders mediated by dysfunctional melanocortin receptor signaling, such as dysfunctional MC4R signaling. In one example, obesity treatable by administration of pharmaceutical compositions including a positive allosteric modulator of melanocortin receptors includes severe or morbid obesity caused by MC4R-haploinsufficiency. In another example, obesity or an obesity-related disorder treatable by the present disclosure can be caused by inadequate production of one or more melanocortin receptor agonists.

As used herein, the term "disease mediated by dysfunctional melanocortin receptor signaling" can refer to a disease that involves dysfunction of activity of a melanocortin receptor, a signal transduction pathway associated with a melanocortin receptor, or an activity or signal transduction pathway that is mediated by a melanocortin receptor. Thus, a disease mediated by dysfunctional melanocortin receptor signaling can include a disease where a melanocortin receptor activity or signal transduction pathway can be modulated for treatment of the disease. More particularly, the present disclosure encompasses compositions and methods that modulate a melanocortin receptor activity and/or melanocortin receptor signal transduction pathway(s) to provide a therapeutic benefit or therapeutic activity for treatment of a disease, such as severe or morbid obesity caused by melanocortin obesity syndrome.

The melanocortin-4 receptor acts as a control for energy storage. Thus, in certain aspects, treating severe or morbid obesity caused by haploinsufficiency of the MC4R may be compared to other syndromes of hormone insufficiency, where the goal is to restore functioning of the signaling pathway to normal levels to reverse the disease. In other aspects, administration of positive allosteric modulators (or any analog or homolog thereof) may increase MC4R receptor sensitivity to αMSH (as compared to a control) and thereby increase the level of MC4R signaling (e.g., from the roughly 50% level seen in MC4R-haploinsufficiency) to normal or wild-type levels. Increasing MC4R receptor sensitivity to αMSH may be engendered by one or combination of pharmacological mechanisms. In one example, a positive allosteric modulator (or any analog or homolog thereof) may inhibit or mitigate MC4R desensitization by inhibiting β-arrestin coupling. In another example, a positive allosteric modulator (or any analog or homolog thereof) may additionally or alternatively activate G protein coupling without inhibiting or blocking MC4R desensitization. In either case, and as opposed to orthosteric modulators, the positive allosteric modulators of the present disclosure can increase MC4R signaling without unwanted pressor side effects, thereby restoring function of one or more GPCR signaling pathways that regulate body weight versus blood pressure.

In some embodiments, the positive allosteric modulators of melanocortin receptor activity described herein are used to treat obesity, including severe and morbid obesity. As used herein, the term "obesity" can refer to a medical condition in which excess body fat has accumulated to the extent that it may have an adverse effect (both physical and mental) on health, leading to reduced life expectancy and/or increased health problems. The obesity can be the result of anything that leads to the accumulation of excess body fat, such as dietary obesity. Body mass index (BMI), a measurement which compares weight and height (calculated from an subject's weight divided by the square of the height), defines subjects as overweight (pre-obese) when their BMI is between 25 kg/m$^2$ and 30 kg/m$^2$, and obese when it is greater than 30 kg/m$^2$. Obesity can also be defined as a condition whereby a subject with at least one co-morbidity has a BMI greater than or equal to 27 kg/m$^2$. An "obese subject" can be an otherwise healthy subject with a BM) greater than or equal to 30 kg/m$^2$, or a subject with at least one co-morbidity with a BMI greater than or equal to 27 kg/m$^2$. The skilled artisan will appreciate that the BMI-based definition of obesity may be modified to reflect changes in understanding of the condition or practices in the field. The skilled artisan will also appreciate that other methods of measurement may be used to define obesity. For example, obesity can be defined in terms of body fat percentage, which can be quantified by a variety of means recognized in the art, such as body average density measurement, bioelectric impedance, skinfold method, height and circumference method, as well as BMI.

As used herein, the terms "severe obesity" and "morbid obesity" can refer to subjects who are about 50% to 100%—or 100 pounds above—their ideal body weight. Alternatively, a BMI value greater than 39 may be indicative of severe or morbid obesity.

In some embodiments, the positive allosteric modulators of melanocortin receptor activity described herein are used to treat an obesity-related disorder. As used herein, the term "obesity-related disorder" can refer to any disorder associated with obesity, such as atherosclerosis, insulin resistance, type 2 diabetes, hypertension, hyperlipidemia, hypertriglyceridemia, cardiovascular disease, microangiopathy in obese individuals with type 2 diabetes, ocular lesions associated with microangiopathy in obese individuals with type 2 diabetes, renal lesions associated with microangiopathy in obese individuals with type 2 diabetes, metabolic syndrome, syndrome X, a fatty liver, fatty liver disease, polycystic ovarian syndrome, hemochromatosis and acanthosis nigricans.

Assays and Modulation of Melanocortin Receptor Activity

Figure 5:
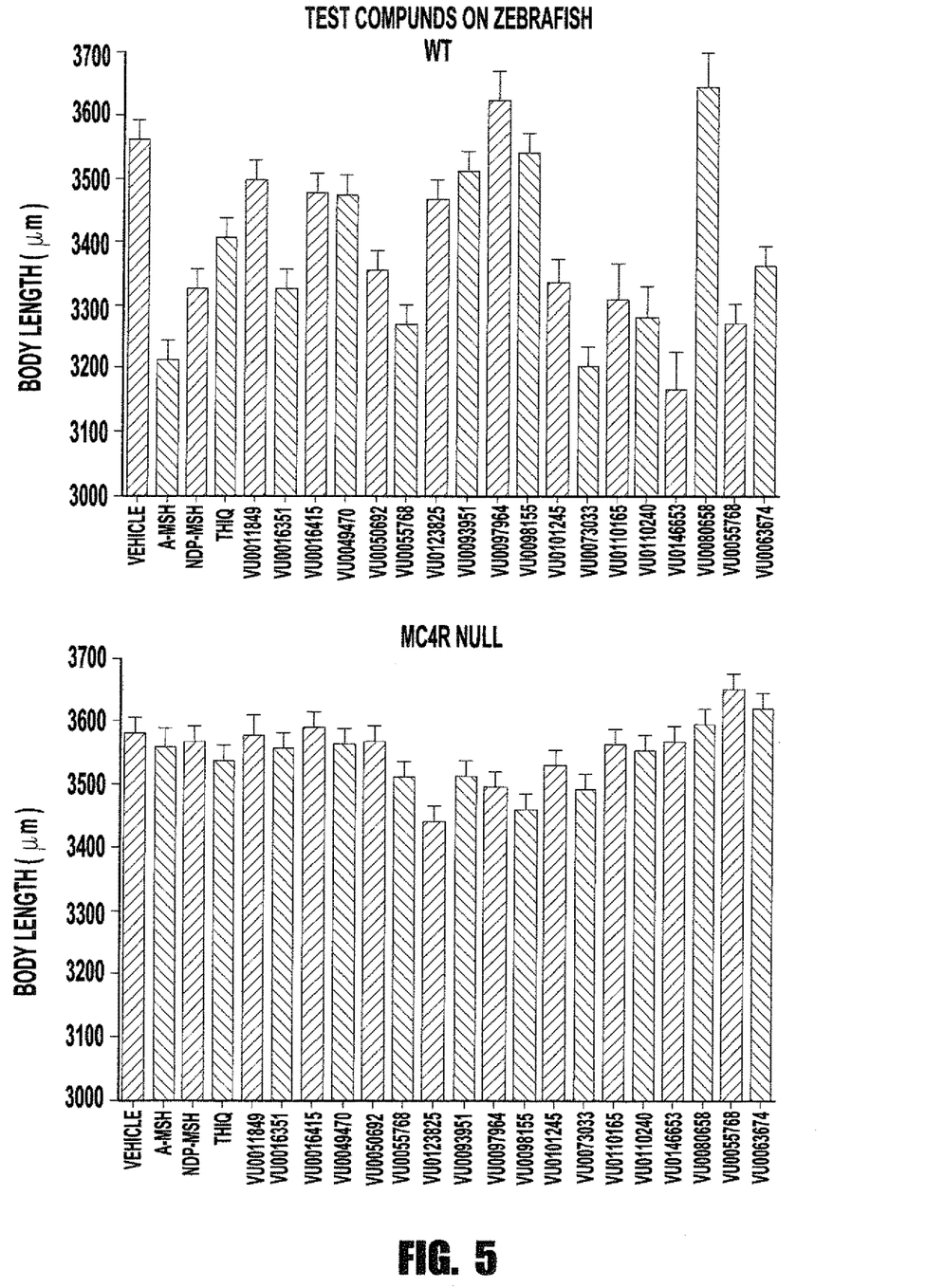
FIG. 5 provides graphs shown the activity of indicated MC4R PAM compounds and control agonists at the MC4R in vivo using a zebrafish growth assay. The MC4R regulates both adiposity and somatic growth in all vertebrates tested.

The positive allosteric modulator compounds of groups I, II and III described herein can also be used to affect melanocortin receptor activity. In one aspect, a method of activating a melanocortin receptor by positive allosteric modulation is provided that includes the step of contacting a melanocortin receptor with a compound of group I or group IL In another aspect, a method of blocking coupling of a melanocortin receptor to β-arrestin is provided that includes the step of contacting a melanocortin receptor with a compound of group III. The ability of the compounds of groups I and III to modulate melanocortin receptor activity were identified by following the drug discovery program shown in FIG. 1. The compounds of group II, on the other hand, were identified on the basis of in vivo activity using the zebrafish assay described herein.

Use of the compounds of groups 1, II and III to affect melanocortin receptor activity includes the step of contacting a melanocortin receptor with a compound of group I, group II, or group III. In specific embodiments, the melanocortin receptor can be a melanocortin-3 receptor (MC3R) or a melanocortin-4 receptor (MC4R). Contacting, as used herein, refers to playing the positive allosteric modifying compound in an environment at a concentration and proximity such that it can be expected to contact the melanocortin receptor and thereby allosterically modify its activity. The melanocortin receptor can be present on a cell, such as a cell of the central nervous system. The melanocortin receptor can also be contacted by the positive allosteric modulator either in vitro, ex vivo, or in vivo. When the melanocortin receptor is contacted in vivo, it may be present in a subject or patient, such as a human subject. It may be desirable to contact melanocortin receptors with compounds of the present invention for research purposes, to provide a therapeutic effect, or for a variety of other reasons.

Figure 4:
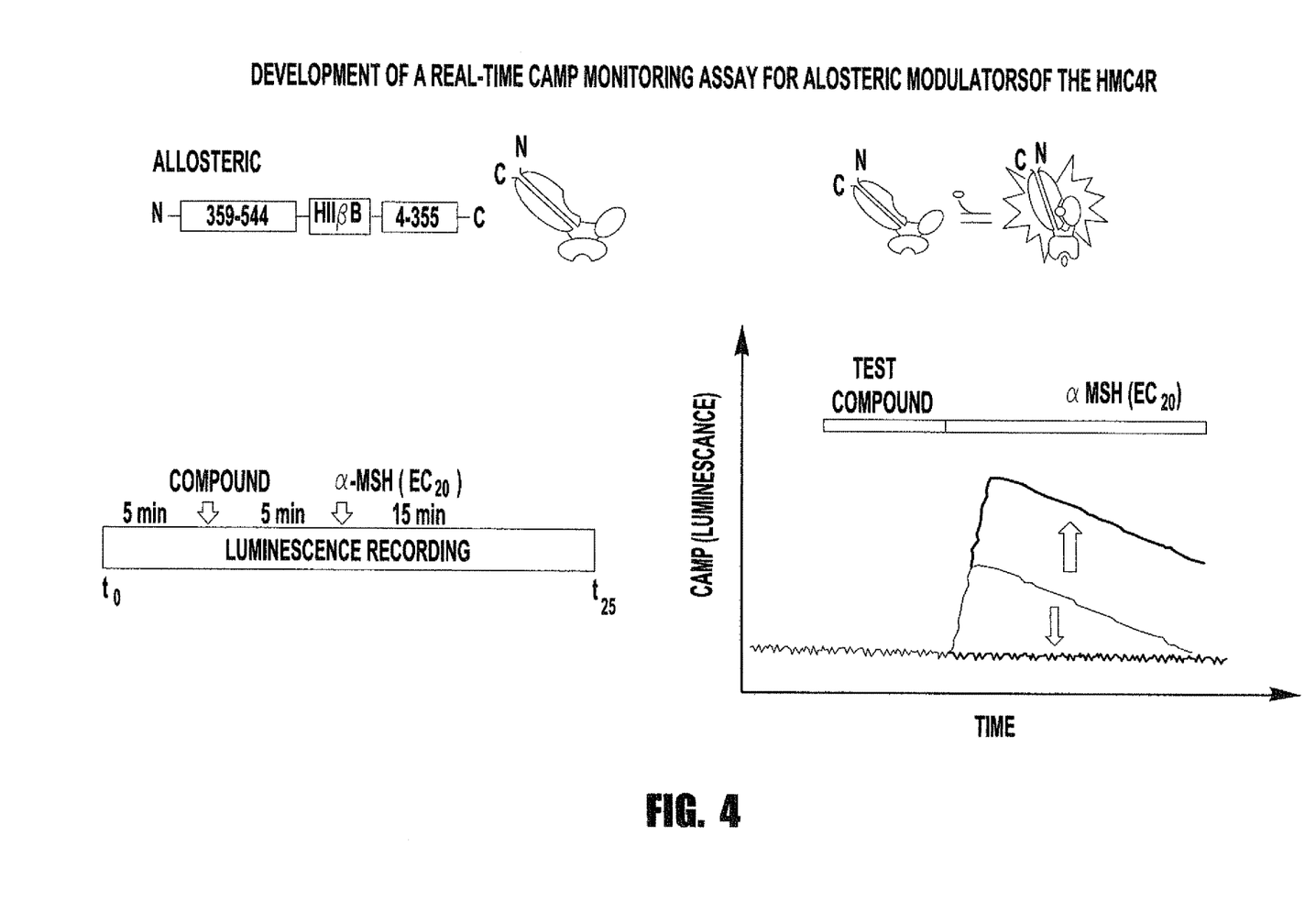
FIG. 4 provides a schematic representation of the HTS assay used to identify MC4R PAMS using a pGLO reporter to record ability of library compounds to enhance the cellular response to an EC20 dose of α-MSH.

In another aspect of the present invention, a method is provided for characterizing a compound that modulates melanocortin receptor activity. The method can include the steps of: (a) providing a population of cells expressing at least one melanocortin receptor, the cells being disposed in a vessel containing a luminescent substrate; (b) contacting the cell population with a test compound; (c) contacting the cell population with a melanocortin receptor agonist; and (d) determining a cAMP response profile for the test compound; wherein the cAMP response profile is indicative of whether the test compound is inactive, orthosteric, allosteric or inhibitory. An overview of this method is provided in FIG. 4.

In some instances, the method can include a high-throughput 384 plate kinetic assay for MC4R function as described in Pantel et al., Eur J Pharmacal 660:139-147 (2011). For example, HEK293 cells stably expressing hMC4R and a fluorescent cAMP reporter (e.g., the PROMEGA PGLO cAMP report, Promega Corporation, Madison, Wis.) can be seeded in 384 well plates. Each cell-containing well, which can be preloaded with the luminescent substrate, can be injected first with a test compound. After about five minutes, a melanocortin receptor agonist (e.g., αMSH) can be administered to each cell-containing well at a partially active $EC_{20}$ concentration. Next, a cAMP response profile can be determined for the tested compound. For example, the cAMP response profile can allow identification and classification of tested compounds as inactive, orthosteric, allosteric or inhibitory. In one example, the assay can be used to identify a positive allosteric modulator, such as those disclosed herein.

One aspect of the invention provides a method of blocking coupling of a melanocortin receptor to β-arrestin. β-arrestin can be assayed using the commercially available PathHunter™ β-arrestin recruitment assay.

On the first day of the assay, thawing and plating frozen PathHunter™ eXpress cells from freezer vials is carried out. The optimized cell culture (OCC) medium is prewarmed in a 37° C. water bath. Cell vial(s) are removed from −80° C. or liquid $N_2$ vapor plate storage and place immediately on dry ice prior to thawing, without exposing the vials to room temperature. The cell vial(s) are then briefly (10 seconds to 1 min) placed in a 37° C. water bath until only small ice crystals remain and the cell pellet(s) is almost completely thawed. Next, 0.5 mL of pre-warmed OCC medium is added to the cell vial. Pipette up and down gently several times to ensure that the cells are evenly distributed, and immediately transfer the cells to 11.5 mL of pre-warmed OCC medium and pour into a disposable reagent reservoir. Then plate 100 µL of cells into each well of the provided 96-well tissue culture plate. After seeding the cells into the microplate, place it into a 37° C., 5% $CO_2$ in a humidified incubator for 24-48 hours prior to testing.

After 24-48 hours have passed, the test compound (i.e., a positive allosteric modulator of group I, II, or III) is dissolved in OCC media. The concentration of the compound should be 22× of the final screening concentration (220 µM). The PathHunter™ eXpress cells (previously plated on day 1) are then removed from the incubator. Transfer 5 µL of the compounds to each appropriate well, and incubate for 5 minutes at 37° C.

The agonist compound is then prepared and added. First, prepare a 22×$EC_{100}$ concentration (2.2 µM) of the agonist. Next, 5 µL of agonist compound is added to each well, and incubated for 90 minutes at 37° C. During the incubation period, a working stock of PathHunter™ Detection Reagents can be prepared by mixing 19 parts Cell Assay Buffer, 5 parts Substrate Reagent 1 and 1 part Substrate Reagent 2. Add 55 µL of prepared detection reagent per well and incubate for 60 minutes at room temperature (23° C.). Results are obtained by reading the chemiluminescent signal.

Compounds of the invention may be synthesized by synthetic routes that include processes similar to those well known in the chemical arts. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)). In the present instance, the compounds were obtained from the Vanderbilt Small Molecule Library, which includes over 160,000 compounds obtained from ChemDiv and ChemBridge.

The present invention is illustrated by the following examples. It is to be understood that the particular examples, materials, amounts, and procedures are to be interpreted broadly in accordance with the scope and spirit of the invention as set forth herein.

EXAMPLES

Example 1: Zebrafish Assay for Melanocortin 4 Receptor Activation

To activate MC4R in vivo in the fish, the endogenous MC4R antagonist, AgRP, must first be inhibited by injection of specific antisense morpholino oligonucleotide. Antisense morpholino oligonucleotide (MO) against the ATG translation initiation site of zebrafish agrp was designed and synthesized from GeneTools. Morpholino oligonucleotide was dissolved in nuclease-free water and stored in −20° C. as 1 mM stock. 0.1 mM working dilution was made using nuclease-free water with 20% Phenol Red (Sigma, 0.5% in DPBS, sterile filtered, endotoxin tested). Before the injection, MO was denatured at 65° C. for 5 min and quickly spun to avoid the formation of aggregates. 5 µL was loaded into a capillary, needle on a micro-injection machine. WT or MC4R null zebrafish embryos at one or two cell stages were injected with 2 nL of 0.1 mM agrp morpholino solution (~2.0 ng per egg).

To test activity of compounds at the MC4R in vivo, following MO injections, embryos were raised in egg water (0.03% ocean sea salt and 0.2 ppm methylene blue in distilled water) in 10 cm petri-dishes at 28° C. Unfertilized dead embryos were excluded at 24 hpf (hour post fertilization). In the following afternoon, at 30 hpf, embryos were removed from their chorions by placing in 0.5 mg/ml of pronase made of egg water for 5 minutes at room temperature. Dechorionation was finished by gentle trituration using a Pasteur pipette. Embryos were rinsed 5-6 times in fresh egg water and 45 live embryos were transferred into single well on a 12-well cell culture plate in 4 ml fresh egg water. 10 mM stock compound solutions were prepared in 100% DMSO. Peptides were dissolved in distilled water and 100 µM stock solutions were made in water with 10% DMSO. A 4 µL compound solution or 40 µL peptide solution was added and mixed into each well to make 10 uL final concentration with 0.1% DMSO. Wells with 0.1% DMSO or 10 µM α-MSH were included as vehicle or positive controls, respectively. Compound/peptide solutions were changed daily.

Embryos were raised under standard light/dark cycle at 28° C. Dead embryos were excluded whenever seen in each well. At 5 dpf (days post fertilization), fish were anaesthetized in 0.4% Tricaine solution and the linear body lengths (forehead to trunk terminus) of 30-35 fish from each well were measured using the axiovision (Ver3.1) digital micrometer with a StemiSV11 Dissecting Microscope (Carl Zeiss INC.). Prism 5.0 was used for the interpretation and analysis of all measurements. The results are shown in FIG. 5, which demonstrate the ability of a number of compounds to decrease zebrafish growth as a result of melanocortin 4 receptor activation. For additional discussion of the use of zebrafish to measure the melanocortin receptor activation, see Zhang et al., Cell Metabolism, 15, 109 (2012), this disclosure of which is incorporated herein by reference.

Example 2: Treatment of a Mouse with a Melanocortin Receptor Activator

Figure 6:
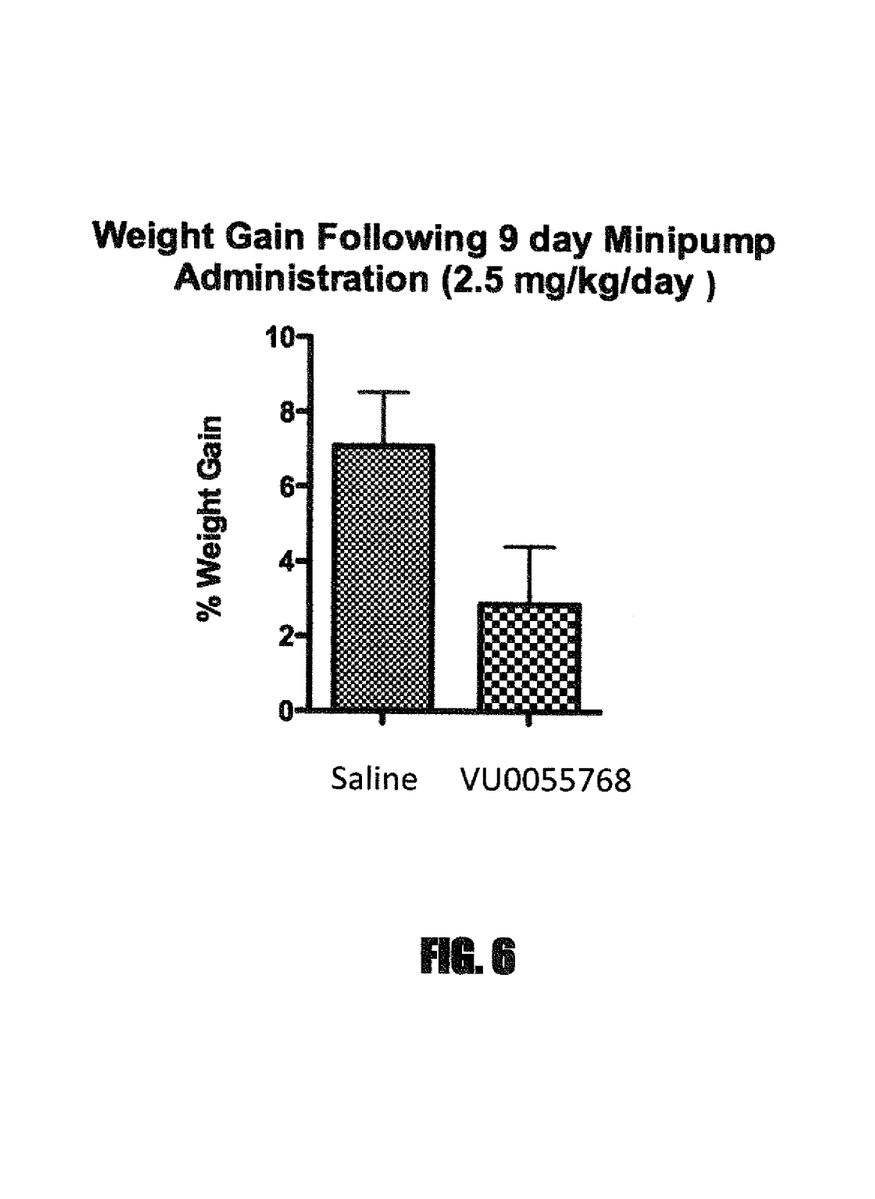
FIG. 6 provides a bar graph showing a reduction in high fat diet-induced weight gain in mice by treatment with VU0055768. Wild type 12 week old male C57BL/6J mice were placed on a high fat diet for 5 days. Mice were then implanted subcutaneously with Alzet osmotic minipumps filled with vehicle (25% DMSO, 25% saline, 50% EtOH; n=6) or VU0055768 (25% compound in DMSO, 25% saline, 50% EtOH, n=5) so as to deliver 2.5 mg/kg/day of VU0055768. Mice were maintained on ad libitum access to water and high fat chow, and body weights were measured at the end of an additional 9 days. Bars indicate the mean and standard error of the data, and show a greater than 50% reduction in weight gain as a result of treatment with VU0055768

An experiment was carried out to demonstrate the effect of treatment of mice with the melanocortin receptor activator VU 0055768. Eleven 12 weeks old Wt C57 mice were placed on high fat diet for 5 days. Osmotic pumps were filled with vehicle (25% DMSO, 25% saline, 50% EtOH) or VU0055768 (25% compound in DMSO, 25% saline, 50% EtOH) as to deliver 2.5 mg/kg/day, and were then inserted subcutaneously (6 vehicle, 5 compound) into the mice. The mice were fed ad-libidum with high fat diet. Mouse and food weight was measured daily. Statistical analysis of the results was t-test. The results are shown in FIG. 6, which shows that mice fed VU 0055768 showed significantly reduced weight gain.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while various theories are presented describing possible mechanisms through with the positive allosteric modulators are effective, the positive allosteric modulators are effective regardless of the particular mechanism employed and the inventors are therefore not bound by theories described herein. The invention is not limited to the exact details shown and described, for variations obvious to one skilled in the art will be included within the invention defined by the claims.

What is claimed is:

1. A method for treating obesity in a subject, comprising administering a therapeutically effective amount of a pharmaceutical composition to the subject including a compound selected from the group consisting of

VU 063674

,

VU 0127431

-continued

VU 0128769

VU 0129567 and pharmaceutically acceptable salts thereof, and a pharmaceutically acceptable carrier.

2. The method of claim 1, wherein the obesity is dietary obesity.

3. The method of claim 1, wherein the obesity is mediated by dysfunctional melanocortin receptor signaling.

4. The method of claim 3, wherein the obesity is mediated by dysfunctional melanocortin-4 receptor (MC4R) signaling.

5. The method of claim 1, wherein the obesity is severe or morbid obesity due to MC4R haploinsufficiency.

6. The method of claim 5, wherein the obesity is melanocortin obesity syndrome.

7. The method of claim 1, wherein the compound is

VU 0127431 and pharmaceutically acceptable salts thereof.

8. The method of claim 1, wherein the compound is

VU 063674 and pharmaceutically acceptable salts thereof.

9. The method of claim 1, wherein the compound is

VU 0128769 and pharmaceutically acceptable salts thereof.

10. The method of claim 1, wherein the compound is

VU 0129567 and pharmaceutically acceptable salts thereof.

* * * * *

UNITED STATES PATENT AND TRADEMARK OFFICE
CERTIFICATE OF CORRECTION

PATENT NO. : 9,744,171 B2  
APPLICATION NO. : 14/383715  
DATED : August 29, 2017  
INVENTOR(S) : Roger D. Cone et al.

Page 1 of 1

It is certified that error appears in the above-identified patent and that said Letters Patent is hereby corrected as shown below:

On the Title Page

Item (72) Inventors:  
Reads "Padma S. Portonova, Brentwood, TN (US)"  
Should read --Padma S. Portonovo, Brentwood, TN (US)--

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*